(12) United States Patent
Zoffmann Jensen et al.

(10) Patent No.: US 8,354,102 B2
(45) Date of Patent: Jan. 15, 2013

(54) ANTIBODIES DIRECTED TO MGLUR7

(75) Inventors: Sannah Zoffmann Jensen, Basel (CH); Hugues Matile, Basel (CH); Christoph Ullmer, Fischingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 188 days.

(21) Appl. No.: 12/599,698

(22) PCT Filed: May 8, 2008

(86) PCT No.: PCT/EP2008/003689
§ 371 (c)(1),
(2), (4) Date: Nov. 20, 2009

(87) PCT Pub. No.: WO2008/138536
PCT Pub. Date: Nov. 20, 2008

(65) Prior Publication Data
US 2010/0303802 A1    Dec. 2, 2010

(30) Foreign Application Priority Data

May 15, 2007    (EP) .................... 07108213

(51) Int. Cl.
*A61K 39/395*  (2006.01)
*C07K 16/18*  (2006.01)
(52) U.S. Cl. ............... 424/130.1; 424/178.1; 530/387.1
(58) Field of Classification Search .................. None
See application file for complete search history.

(56) References Cited

U.S. PATENT DOCUMENTS 5,738,999 A    4/1998  Segerson
7,253,257 B2   8/2007  Flor et al.

FOREIGN PATENT DOCUMENTS

WO    WO 2005/075988 A    8/2005

OTHER PUBLICATIONS

Song et al., Antibody mediated in vivo delivery of small interfering RNAs via cell-surface receptors. Nature Biotechnology 23:709-717, 2005.*
Blanpain Cedric et al: *Molecular Biology of the Cell*, (2002) vol. 13, 723-737.
Tolbert Lara M et al: *Journal of Neurochemistry*, Philadelphia (1998), vol. 70, 113-119.
Makoff et al., *Molec. Brain Res.* 40:165-170 ( 1996).
Wu,S. et al., *Molec. Brain Res.* 53:88-97 ( 1998).
Okamoto et al., *J. Biol.Chem* 269:1231-1236 ( 1994).
(Translation of Jap Off Act in Corres Jap Appl 2010507829 Jul. 25, 2012).
Phillips et al., Molecular Brain Research 57(1):132-141 ( 1998).
Database WPI Week 200436, *Thomson Scientific*, London, GB; AN 2004-381452 XP002500166.
Acris Antibodies: "Polyclonal Antibody to human G protein-coupled receptor GPR87/GPR95" *Internet Citation*, (online) XP002419109, 2004.
Haasen Dorothea et al: *Methods in Enzymology* (2006), vol. 414, 2006, pp. 121-139, XP009107255.
Liu Bin: *Briefings in Functional Genomics and Proteomics*, , vol. 6.2, 31 (2007), pp. 112-119, XP009107654.
Bradley S R et al: *The Journal of Neuroscience: The Official Journal of the Society for Neuroscience* (1996), 16:6, pp. 2044-2056, XP002500164.
Sahara Y et al: *Neuroscience Letters*, ( 2001), 312:2, pp. 59-62, XP002500165.

* cited by examiner

*Primary Examiner* — Ruixiang Li
(74) *Attorney, Agent, or Firm* — George W. Johnston; Dennis P. Tramaloni; Brian C. Remy (57) ABSTRACT

The present invention provides an antibody directed to an epitope of a G-protein coupled receptor, wherein the antibody binds to the extracellular N-terminal region of the receptor and the binding of the antibody to the G-protein coupled receptor induces receptor internalization in cells.

4 Claims, 7 Drawing Sheets

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'Cy5
<220> FEATURE:
<221> NAME/KEY: modified_base
<222> LOCATION: (1)..(3)
<223> OTHER INFORMATION: 2'OMe nucleotide
```

```
<220> FEATURE:
<221> NAME/KEY: modified_base
<222> LOCATION: (5)..(5)
<223> OTHER INFORMATION: 2'OMe nucleotide
<220> FEATURE:
<221> NAME/KEY: modified_base
<222> LOCATION: (7)..(8)
<223> OTHER INFORMATION: 2'OMe nucleotide
<220> FEATURE:
<221> NAME/KEY: modified_base
<222> LOCATION: (12)..(12)
<223> OTHER INFORMATION: 2'OMe nucleotide
<220> FEATURE:
<221> NAME/KEY: modified_base
<222> LOCATION: (14)..(17)
<223> OTHER INFORMATION: 2'OMe nucleotide
<220> FEATURE:
<221> NAME/KEY: modified_base
<222> LOCATION: (20)..(22)
<223> OTHER INFORMATION: dT
<220> FEATURE:
<221> NAME/KEY: misc_feature
<222> LOCATION: (21)..(22)
<223> OTHER INFORMATION: C6SSC6 linkage

<400> SEQUENCE: 1
cuuacgcuga guacuucgat tt                                              22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'OMe nucleotide
<220> FEATURE:
<221> NAME/KEY: modified_base
<222> LOCATION: (11)..(11)
<223> OTHER INFORMATION: 2'OMe nucleotide
<220> FEATURE:
<221> NAME/KEY: modified_base
<222> LOCATION: (16)..(16)
<223> OTHER INFORMATION: 2'OMe nucleotide
<220> FEATURE:
<221> NAME/KEY: modified_base
<222> LOCATION: (20)..(21)
<223> OTHER INFORMATION: dT
<220> FEATURE:
<221> NAME/KEY: misc_feature
<222> LOCATION: (20)..(21)
<223> OTHER INFORMATION: Phosphorothioate linkage

<400> SEQUENCE: 2
ucgaaguacu cagcguaagt t                                               21
```

ANTIBODIES DIRECTED TO MGLUR7

This application is the National Stage of International Application No. PCT/EP2008/003689 filed May 8, 2008, which claims the benefit of EP 07108213.5 filed May 15, 2007, which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Nov. 1, 2012, is named 24272.txt and is 1,862 bytes in size.

The present invention relates to an antibody directed to G-protein coupled receptors (GPCR), in particular to metabotropic glutamate receptors.

GPCRs are one of the largest receptor superfamilies known. These receptors are biologically important and malfunction of these receptors results in diseases such as Alzheimer's, Parkinson, diabetes, dwarfism, color blindness, retinal pigmentosa and asthma. GPCRs are also involved in depression, schizophrenia, sleeplessness, hypertension, anxiety, stress, renal failure and in several other cardiovascular, metabolic, neural, oncology and immune disorders (F. Horn and G. Vriend, J. Mol. 25 Med., 76: 464-468 (1998)). They have also been shown to play a role in HIV infection (Y. Feng et al., Science, 272: 872-877 (1996)). The structure of GPCRs consists of seven transmembrane helices that are connected by loops. The N-terminus is always extracellular and C-terminus is intracellular. GPCRs are involved in signal transduction. The signal is received at the extracellular N-terminus side. The signal can be an endogenous ligand, a chemical moiety or light. This signal is then transduced through the membrane to the cytosolic side where a heterotrimeric G-protein is activated which in turn elicits a response (F. Horn et al., Recept. and Chann., 5: 305-314 (1998)).

It is an object of the present invention to provide an antibody directed to an epitope of a G-protein coupled receptor wherein the antibody binds to the extracellular N-terminal region of the receptor and the binding of the antibody to the G-protein coupled receptor induces receptor internalization in cells.

In a preferred embodiment the antibody is directed to a GPCR class C receptor, preferably a metabotropic glutamate receptor, in particular to the metabotropic glutamate receptor mGluR7.

In a further embodiment, the antibody is a monoclonal antibody.

In a further preferred embodiment, the antibody induced receptor internalisation does not depend on the activation of the G-protein mediated signalling pathway associated with the receptor, preferably the Gi coupled cAMP signalling pathway associated with the receptor. In a further preferred embodiment, the antibody induced receptor internalisation involves the mitogen-activated protein kinase (MAPK) signalling pathway.

In a further embodiment, the antibody has been produced by immunizing suitable animals with whole cells expressing the G-protein coupled receptor of interest, preferably mGluR7.

In a further preferred embodiment, the antibody is produced by hybridoma cell line mGluR7-CHO-1/28 which was deposited with the DSMZ (German Collection of Microorganisms and Cell Cultures) on Aug. 8, 2007 and received the deposit number: DSM ACC2855.

In a second object, the present invention relates to the use of the antibody of the present invention for the manufacturing of a medicament for the treatment of a disease involving modulation of a G-protein coupled receptor signalling pathway. The disease is preferably a neurological disorder or diabetes.

In a further embodiment, the antibody of the present invention is used as a tool for the intracellular delivery of active compounds. The active compound is preferably covalently coupled to the antibody. The "active compound" can be any suitable molecule, including DNA, RNA, siRNA, a protein, a peptide, or a pharmaceutically active agent, such as, for example, a toxin, an antibiotic, an antipathogenic agent, an antigen, an antibody, an antibody fragment, an immunomodulator, an enzyme, or a therapeutic agent. The antibody of the present invention is suitable for intracellular delivery of active compounds since the antibody allows a targeted intracelluar delivery of the active compounds by binding to the GPCR.

In a third object, the present invention relates to a method for screening for ligands of a G-protein coupled receptor. The method comprises:
a) contacting cells expressing the G-protein coupled receptor or a cellular preparation comprising the G-protein coupled receptor with a compound to be screened and the antibody of the present invention, and
b) measuring antibody interaction with the G-protein coupled receptor, wherein the level of antibody binding or internalisation is indicative for a ligand/G-protein coupled receptor interaction.

In a preferred embodiment, the cells stably express the G-protein coupled receptor.

In a further preferred embodiment, the G-protein coupled receptor is metabotropic glutamate receptor, preferably mGluR7.

The term "Antibody" as used herein encompasses an antibody or antibody fragment including but not limited to antibody fragments such as Fv, Fab, F(ab')$_2$, single chain antibody.

In a further object, the present invention provides a conjugate comprising an antibody of the present invention and an active compound covalently linked to the antibody.

In a preferred embodiment, the active compound is a toxin or a siRNA molecule, preferably a siRNA molecule.

A method of preparing an siRNA-antibody conjugate in the form A-X-Y by covalently bonding the antibody of the present invention to an end group of an siRNA molecule, the method comprising: selecting a predetermined siRNA molecule; and covalently bonding the siRNA molecule to the antibody of the present invention, wherein A is the antibody of the present invention, X is a linker-mediated covalent bond, and Y is an siRNA molecule.

The method of preparing a siRNA-antibody conjugate can comprise activating a functional group of siRNA, and covalently bonding the activated functional group to the antibody. The functional group to be activated can include, but is not limited to, an amine group, thiol group, phosphate group, or combinations thereof. In some embodiments, the material which activates the functional group of siRNA comprises 1-ethyl-3,3-diethylaminopropyl carbodiimide, imidazole, N-hydroxylsuccinimide, dichlorohexylcarbodiimide, N-β-maleimidopropionic acid, N-β-maleimidopropyl-oxylsuccinimide ester, N-succinimidylpyridyldithiopropionate, or combinations thereof. Further methods for preparing the siRNA antibody conjugate of the present invention can be found in the Handbook of Cell Penetrating Peptides, Chapter 18, Second Edition, April 2006, Editor: Ülo Langel.

In a further object, the present invention provides a pharmaceutical composition comprising an antibody or a conjugate of the present invention and a pharmaceutically acceptable carrier For better administration, the composition can further comprise at least one kind of pharmaceutically acceptable carrier in addition to the above-described active ingredients. Examples of such carriers include saline solution, sterile water, Ringer's solution, buffered saline solution, dextrose solution, maltodextrin (aqueous) solution, glycerol, ethanol and mixtures thereof. If needed, typical additives, such as, an antioxidant, a buffer, a bacteriostatic agent and the like, can be added. Moreover, the composition can be pharmaceutically produced for injection in the form of an aqueous solution, suspension, emulsion and so forth by adding more additives, such as, a diluting agent, a dispersing agent, a surfactant, a bonding agent and a lubricant.

The pharmaceutical composition of the invention can be brought into contact with the body through diverse administration routes, including intravenous administration, intramuscular administration, intra-arterial administration, intramedullary administration, intrathecal administration, intracardiac administration, percutaneous administration, hypodermic administration, intraperitoneal administration, sublingual administration, and topical administration.

For such clinical administration, the pharmaceutical composition of the present invention can be prepared in an adequate product using conventional techniques.

SHORT DESCRIPTION OF THE FIGURES

FIGS. 1A-I show a comparison of IgG and Fab1 induced mGluR7 internalization;

FIG. 5 shows the cointernalization of fluorescent siRNA when covalently linked to the IgG. FIG. 5 A-D is with primary antibody labelled with siRNA-Cy5, FIG. 5 E-H with primary antibody mixed with siRNA-Cy5;

The IgG-induced increase of p44/42 MAPK levels is transient reaching a maximal level 5 min after treatment and rapidly declines thereafter.

EXPERIMENTAL PART

EXAMPLE 1

Quantification of Membrane to Cytoplasm Translocation of Receptor with Antibody

Sample Preparation

Day 1: Chinese Hamster Ovarian cells stably expressing the rat mGluR7 receptor were seeded 24 hours prior to the experiment:

Cells were detached with Trypsin/EDTA. Growth medium was added and cells were resuspended by passaging through a 10 ml pipette 10-20 times. Cell concentration was determined and the cell suspension was diluted to a suitable concentration. For an experiment performed in a 96 well plate, the cells were seeded at 25.000 cells/well in 100 µl medium. The cells were incubated at 37° C. in a humidified cell culture incubator with 5% $CO_2$ to allow the cells to adhere to the wells.

Day 2: I-buffer was prepared. (1×HBSS, 20 mM Hepes, 0.1% BSA, prepared with tri-distilled water, pH not adjusted). Hoechst 33258 and TrueBlue Chloride solution was prepared with 37° C. warm I-buffer. During the following additions of solutions, a temperature of 37° C. was maintained in the wells. The cell-culture medium was gently aspirated. In each well, 100 µl Hoechst and Trueblue solution was added and the plate incubated for 30 minutes at 37° C. in humidified incubator.

The antibody/Fab1 solution were prepared and equilibrated at 37° C. for 5 minutes. The cells were washed once carefully and quickly with 100 µl/well of I-buffer pre-equilibrated at 37° C. Then 60 µl/well of the antibody solution was added to the wells and the plate was incubated for 30 minutes at 37° C. temperature.

A 1:400 solution of Alexa532 goat-anti-mouse secondary antibody was prepared with icecold PBS. The wells were washed three times with 100 µl/well PBS at room temperature. The plate was transferred to an icebath, 60 µl/well of the icecold antibody solution was added to the wells and the plate was incubated for 60 minutes. The wells were washed three times with 100 µl/well icecold PBS. 150 µl/well of methanol with a temperature of −20° C. was added pr well and the plate incubated on ice for 10 minutes. The wells were washed with 100 µl/well PBS at room temperature, 100 µl/well of the formaldehyde solution was added to the wells and the plate was incubated for 15 minutes at room temperature. The wells were washed once with PBS at room temperature. The cell membranes were permeabilized by incubation with a 0.25% Triton X-100 solution at RT for 5 minutes. The wells were washed once with PBS and incubated with a 10% vol/vol solution of Goat serum diluted in PBS for 30 minutes. The goat serum was replaced with a freshly prepared 1:400 solution of Alexa647 goat-anti-mouse secondary antibody diluted in PBS. The cells were incubated at RT for 30', washed carefully and quickly three times with 100 µl/well PBS at room temperature. Then 100 µl/well of 4% formaldehyde were added, and the wells were incubated for 15 minutes at room temperature. The solution was replaced with 150 µl PBS/well.

Quantification of Subcellular Level of Immunostain

Internalization of antibody (IgG or Fab 1 fragment) was quantified using an Opera QEHS HCS reader from Evotec Technologies, Hamburg, Germany. This machine is equipped with an inverted confocal fluorescence microscope and is set up to do automated acquisition of images from samples prepared in clear bottom microtiter plates. In the reader, the software "Accapella" for image analysis is integrated, where image analysis methods (scripts) can be prepared, which identifies the localization of predefined types of objects.

The script that was used for the quantification in this example was developed to identify the intensity of immuno stain respectively on the cell surface and localized in intracellular compartments (recognized as spot like structures which are not co-localized with cell surface immunostain). The analysis is based on three images acquired in parallel of samples stained with a DNA-specific fluorophore, the homogenous intact cell stain TrueBlue, and two secondary antibodies with different conjugated fluorophores. From each image, objects are identified. From the first image specific for the DNA stain and Trueblue stain, the number, position, size and shape of the nuclei was determined from the brighter hoechst stain, and the outline of the cytoplasm from the Trueblue stain. From the second image selective for Alexa532 secondary antibody, the areas with cell surface immunostaining was determined and the intensity quantified. From the third, spot like structures in the cytoplasm of the cells was identified and the fluorescence intensity quantified.

Comparison of IgG and Fab1 Fragment Induced mGluR7 Internalization

Figure 1A:
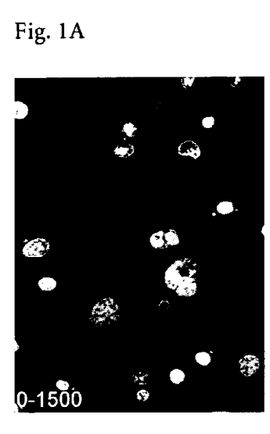

FIG. 1 shows images of rat-mGluR7 expressing cells which have been incubated with 67 nM primary antibody, fab1 fragments or buffer at 37° C. before washed and transferred to ice for secondary staining and fixation as described in the protocol. Each row contains images acquired in parallel of the same field of view in the well. Panel A-C is with 33 nM primary antibody, panel D-F with 67 nM fab1 fragment and Panel G-I, with no primary antibody or fab1 fragments. Panel A, D and G show images acquired with filtersettings selective for trueblue and hoechst stain: Laser 405 nm, emission reflected by Longpath 650 filter, filtered through Shortpath 568 filter and Bandpath 455/70 filter. Panel B, E and H show images acquired with filtersettings selective for the cell surface stain with Alexa532 secondary antibody: Laser 532 nm, emission reflected by LP650 and filtered through LP568 and BP586/40. Panel C, F and I show images acquired with filtersettings selective for the whole cell stain with Alexa647 secondary antibody after membrane permeabilization: Laser 635 nm, emission passing through LP650 and filtered through BP690/50. The range of the pixel intensity greyscale ranging from black to white is indicated in lower left corner of the individual images.

Intact IgG and Fab1 fragments behave differently when incubated with mGluR7 expressing CHO cells at 37° C. The IgG is to a large extent internalized, while the Fab1 fragments almost exclusively is localized at the cell surface.

Figure 2A:
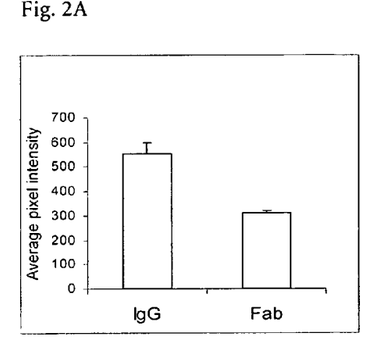
FIG. 2 shows the quantified surface staining and cytoplasmic spot intensity for IgG and Fab1 fragments, respectively, induced mGluR7 internalization.

FIG. 2 shows the quantified surface staining and cytoplasmic spot intensity for respectively IgG and Fab1 fragments. Panel A: Average pixel intensity in cell surface stain. Panel B: Pixel intensity in Cytoplasmic spots pr cytoplasmic area.

Kinetic of IgG and Fab Fragment Induced mGluR7 Internalization

The experiment was carried out according to the protocol, with the following modifications: The cells were incubated with primary antibody or Fab fragments at 37° C. for up to 60 minutes, then transferred to ice and the solutions replaced with fresh icecold solutions of primary antibody or Fab fragments for 1 h prior to staining with secondary antibody. The Trueblue and hoechst staining of the cytoplasm was replaced with a staining step following the formaldehyde fixation, where the samples where incubated with 3 uM Hoechst and 2 µg/ml CellmaskBlue in PBS for 15 minutes at roomtemperature followed by a second fixation with 4% formaldehyde for 15 minutes at roomtemperature.

Figure 3A:
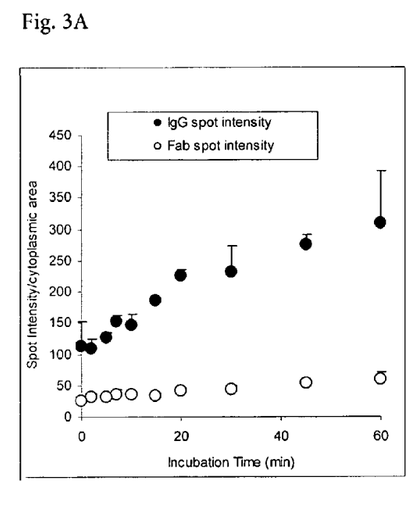
FIG. 3 shows the kinetic of IgG and Fab induced mGluR7 internalization.

FIG. 3 shows the kinectic of binding and uptake of IgG and Fab. Black circles: 22 nM IgG, white circles: 33 nM Fab. The curve is an average of two different experiments+/− Standard deviation, each experiment carried out in triplicates. Panel A: Average pixel intensity in cell surface stain. Panel B: Pixel intensity in Cytoplasmic spots per cytoplasmic area. IgG shows increased accumulation in intracellular spot like structure, with the curve flattening out after the first 20-30 minutes. In comparison a very minor increase is detectable for the Fab fragments.

Effect of Pertussis Toxin on IgG Induced Internalization

The experiment was carried out according to the protocol, with the modification, that at the day of experiment a 20× dilution of pertussis toxin in PBS, to final 500 ng/ml was added to the wells 5 h prior to the incubation with antibodies.

Figure 4A:
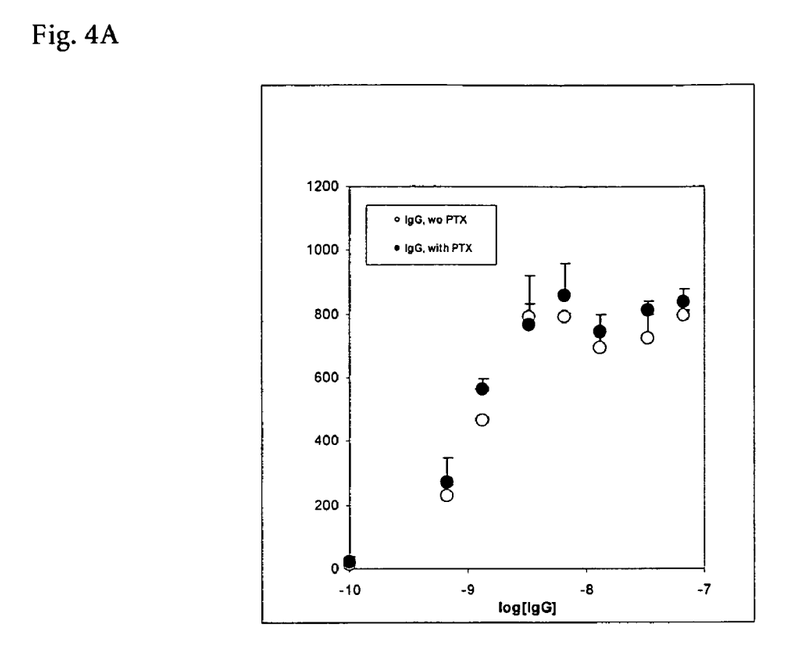
FIG. 4 shows the effect of pertussis toxin on IgG induced mGluR7 internalization; 4A: Average pixel intensity in cell surface stain. 4B: Pixel intensity in Cytoplasmic spots per cytoplasmic area.
Figure 4B:
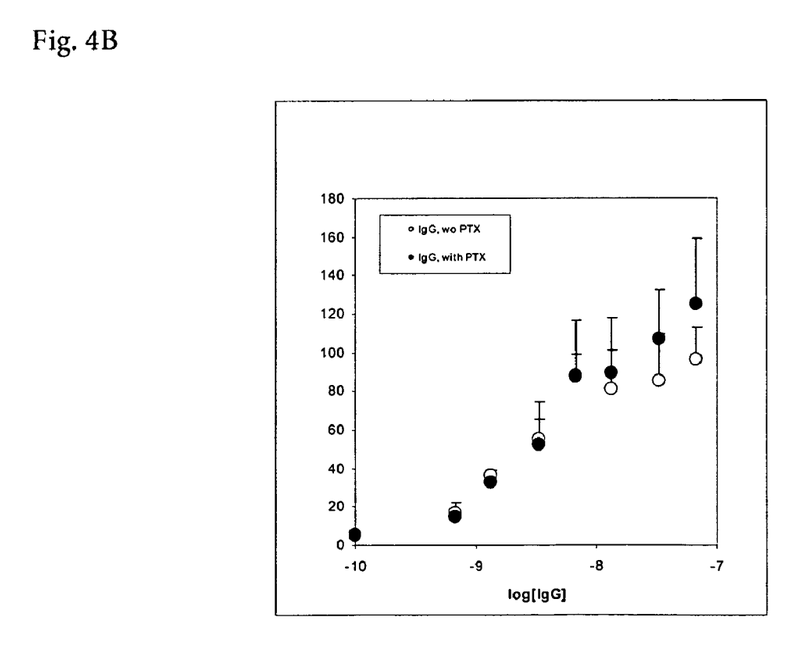

FIG. 4 shows a dose response curve with different concentrations of IgG. Black circles: Pertussis toxin treated cells, white circles: No pertussis toxin. Each point is the average of three wells, +/− Standard deviation. Panel A: Average pixel intensity in cell surface stain. Panel B: Pixel intensity in Cytoplasmic spots per cytoplasmic area. Pertussin toxin pretreatment does not affect the IgG induced internalization of mGluR7 i.e. IgG induced receptor internalisation does not depend on the cAMP signalling cascade of the receptor.

Antibody Mediated Cellular Uptake of siRNA

The experiment was carried out according to the protocol, with the following modifications: The cells were incubated with 67 nm primary antibody conjugated to siRNA-Cy5 (Molar ratio 1 to 0.3) or a mix of 67 nM primary antibody and 20 nM siRNA-Cy5 at 37° C. for 40 minutes. The secondary antibody used for detection of cell surface primary immunostaining was labelled with Alexa488 and the secondary antibody used for detection of whole cell primary immunostaining was labelled with Alexa532. The Trueblue and hoechst staining of the cytoplasm was replaced with a staining step following the formaldehyde fixation, where the samples where incubated with 3 uM Hoechst and 2 µg/ml CellmaskBlue in PBS for 15 minutes at roomtemperature followed by a second fixation with 4% formaldehyde for 15 minutes at roomtemperature.

Figure 5A:
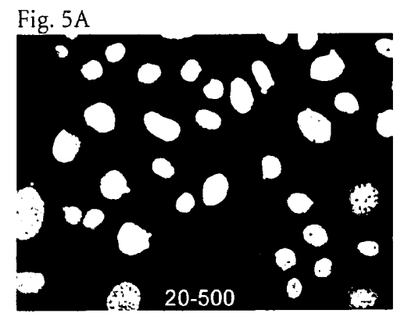

FIG. 5 shows images of rat-mGluR7 expressing cells which have been incubated with primary antibody conjugated to siRNA-Cy5 or a mix of primary antibody and siRNA-Cy5 at 37° C. before staining and fixation as described above. Each row contains images acquired in parallel of the same field of view in the well. Panel A-D is with primary antibody labelled with siRNA-Cy5, panel E-H with primary antibody mixed with siRNA-Cy5.

Panel A and E show images acquired with filtersettings selective for trueblue and hoechst stain: Excitation with Laser 405 nm, emission reflected by Longpath 650 filter, filtered through Shortpath 568 filter and Bandpath 455/70 filter.

Panel B and F show images acquired with filtersettings selective for Cy5: Excitation with laser 635 nm, emission passing through LP650 and filtered through BP690/50.

Panel C and G show images acquired with filtersettings selective for the whole cell stain of primary antibody with Alexa532 secondary antibody: Excitation with Laser 532 nm, emission reflected by LP650 and shortpath 568 and filtered through BP586/40.

Panel D and H show images acquired with filtersettings selective for the cell surface specific stain of primary antibody with Alexa488 secondary antibody after membrane permeabilization: Excitation with Laser 488 nm, emission reflected by LP650 and filtered through Shortpass 568 filter and Bandpath 532/60 filter.

The range of the pixel intensity greyscale ranging from black to white is indicated in the lower part of the individual images.

The IgG can mediate cellular uptake of siRNA. When IgG covalently linked to siRNA-Cy5 is incubated with mGluR7 expressing CHO cells at 37° C., the IgG and siRNA-Cy5 are both internalized and colocalizes in intracellular compartments. Without a covalent link between IgG and siRNA, only the IgG is internalized.

EXAMPLE 2

Generation of Rat mGlu7 Expressing Cell Line

The cDNA of the rat mGlu7a receptor splice variant (Genbank: D16817) was inserted into a eukaryotic expression vector pcDNA3.1(+). This plasmid was transfected into CHO cells deficient in dihydrofolate reductase activity (CHO-dhfr⁻) harboring a luciferase reporter gene under the control of 5 cAMP-responsive elements (CRE) using Lipofectamine plus according to the instruction of the manufacturer. Clones were isolated through limited dilutions and identified by activities in the reporter gene assay. Cells were stimulated with 1 µM forskolin and 0.5 mM L-AP4 in the assay buffer. After 4 h the supernatant was exchanged with lysis buffer and the luciferase activity measured. Responses ranged from no depression to about 83% depression. A clonal cell line displaying the greatest inhibition of forskolin-mediated luciferase activity was selected and identified as giving consistently good responses for up to at least 20 passages.

For whole cell immunization a stable cell line has been transiently transfected again with the expression plasmid for mGlu7 using Lipofectamine plus and frozen for immunizations in liquid nitrogen.

EXAMPLE 3

Whole Cell Immunization

Immunisation of swiss albino mice was performed with stably expressing mGluR7 transfected CHO cells, by repeated injection of living cells. As soon as the animals showed a specific immunoresponse to mGluR7, the spleen cells were removed and fused to Ag8 cells according to G. Köhler and C. Milstein (1975) "Continuous cultures of fused cells secreting antibody of predefined specificity". Nature 256:495-497.

EXAMPLE 4 cAMP Assay

Cells stably expressing the rat mGluR7 receptor are seeded 17-24 hours prior to the experiment in a black 96 well plate with flat clear bottom (Corning Costar #3904) in growth medium with 7.5% dialyzed fetal calf serum and incubated at 5% CO2 and 37° C. in a humidified incubator. The growth medium was exchanged with Krebs Ringer Bicarbonate buffer with 1 mM IBMX and incubated at 30° C. for 30 min. Compound was added for 15 min prior to the addition of 0.3 mM L-AP4 and 3 µM forskolin to a final assay volume of 100 µl and incubated for 30 min at 30° C. The assay was stopped by the addition of 50 µl lysis reagent and 50 µl detection solutions and shaked for 2 h at room temperature.

The time-resolved energy transfer is measured by a plate:: vision TRF reader (Evotec Technologies GmbH, Hamburg Germany), equipped with a ND:YAG laser as excitation source. The plate is measured twice with the excitation at 355 nm and at the emission with a delay of 100 ns and a gate of 100 ns, total exposure time 10 s at 730 (bandwith 30 nm) or 645 nm (bandwith 75 nm), respectively. The measured signal at 730 nm has to be corrected for the ruthenium background, the direct excitation of Alexa and the buffer control. The FRET signal is calculated as follows: FRET=T730-Alexa730-P (T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

Figure 6:
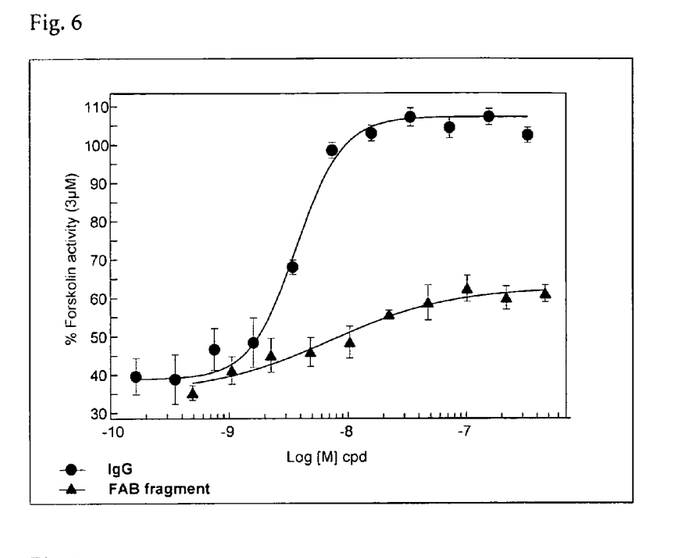
FIG. 6 shows a concentration-response curve of the IgG (filled circle) and FAB (filled triangle) fragments. Cells were stimulated with 3 µM forskolin, an EC80 of L-AP4 and various concentrations of IgG or FAB. The cellular content of cAMP was measured and expressed as cAMP content in percent to cells treated with 3 µM forskolin only. All measurements were performed in triplicates and values represent the means±SE.

FIG. 6 shows a concentration-response curve of the IgG (filled circle) and FAB (filled triangle) fragments. Cells were stimulated with 3 µM forskolin, an EC80 of L-AP4 and various concentrations of IgG or FAB. The cellular content of cAMP was measured and expressed as cAMP content in percent to cells treated with 3 µM forskolin only. All measurements were performed in triplicates and values represent the means±SE. The activity of the orthosteric mGlu7 agonist L-AP4 is completely inhibited by the addition of the IgG. The IC50 is calculated to be 2.4 nM. The FAB is partially antagonizing the agonist L-AP4 (IC50: 486 nM), suggesting the requirement of a bivalent binding mode of the IgG in order to potently antagonize L-AP4 activities.

EXAMPLE 5

Construction of Chimeric Receptors cDNAs encoding chimeric mGlu6 and mGlu7 receptors were constructed using cross-over PCR. The mGlu6/7 receptor construct contains 565 aa derived from the N-terminal extracellular region of the rat mGluR6 and the remaining C-terminal portion of the rat mGluR7a receptor, comprising the entire transmembrane region; the mGluR7/6 construct is essentially the reverse chimera with the fusion point at amino acid 576. The cDNAs were cloned into pcDNA3.1 and transiently transfected into CHO-dhfr-cells using Lipofectamine plus. 24 h after transfection cells were plated onto poly-D-lysine coated cover slips in growth medium and stained the following day. Cells grown in a 24-well plate are placed on ice, IgG or IgG-Alexa488 added (1:100) and incubated for 30 min in DMEM, washed twice with DMEM before the addition of a rabbit-anti mouse FITC antibody (1:100), incubated 30 min still on ice, and after two wash steps as before mounted with glycerol/PBS (1:1).

Figure 7:
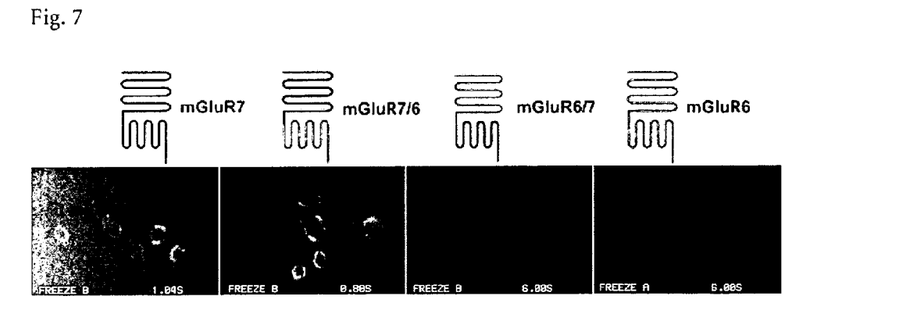
FIG. 7 shows immunostaining of living CHO cells transiently expressing wild type or chimeric mGlu6 or mGlu7 receptors as indicated. Cells were stained with IgG-Alexa488. Only receptors with the N-terminal domain of mGlu7 receptors were recognized by the IgG, suggesting that the IgG binds to the N-terminal domains of mGlu7 receptors. Shown are representative images at 40× magnification with the exposure time in seconds.

FIG. 7 shows immunostaining of living CHO cells transiently expressing wild type or chimeric mGlu6 or mGlu7 receptors as indicated. Cells were stained with IgG-Alexa488. Only receptors with the N-terminal domain of mGlu7 receptors were recognized by the IgG, suggesting that the IgG binds to the N-terminal domains of mGlu7 receptors. Shown are representative images at 40× magnification with the exposure time in seconds.

EXAMPLE 6

IgG-Induced p44/42 MAPK Activities

Cells stably expressing the rat mGluR7 receptor are seeded in growth medium in 6 well plates. The next day, medium is replaced with 2 ml starvation medium (Opti-MEM with 0.1% fatty acid free BSA). The following day cells are stimulated with compound in 150 µl starvation medium for the indicated times at 37° C., otherwise cells are stimulated for 5 minutes. Cells are washed with ice cold PBS and lyzed in 150 ul buffer containing 1 mM β-glycerophosphate 1 mM EDTA, 1 mM EGTA, 1 µg/ml leupeptin, 150 mM sodium chloride, 2.5 mM sodium phosphate, 20 mM Tris-Cl, 1 mM PMSF and 1% Triton X-100, scraped off and sonicated on ice. After centrifugation the supernatant is analyzed for p44/42 MAPK activities using the PathScan™ Sandwich ELISA kit according to instructions of the manufacturer. Absorbance (450 nM) is read using the EnVision reader (Perkin Elmer).

Figure 8A:
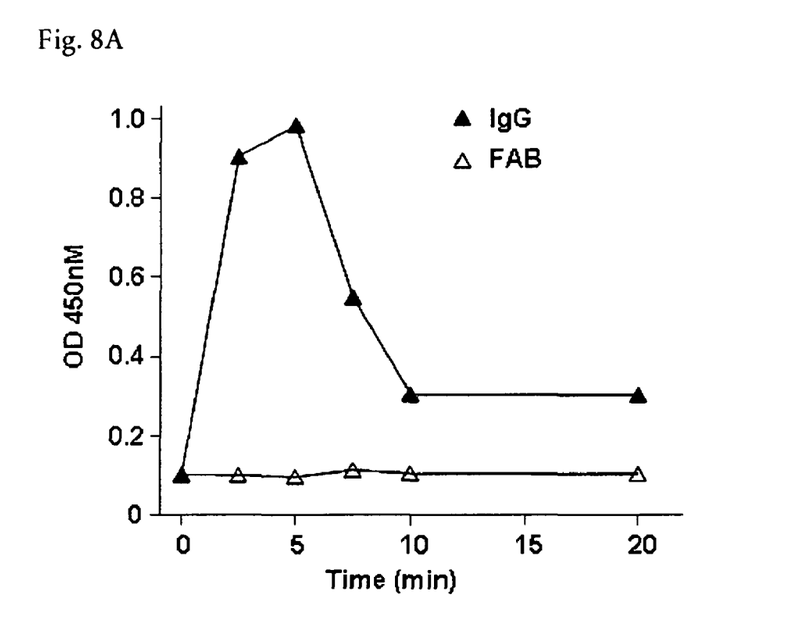
FIG. 8A shows the effect of IgG on the levels of p44/42 MAPK at Thr202/Tyr204 in CHO cells expressing mGlu7 receptors. The p44/42 MAPK levels were determined by means of PathScan™ Sandwich ELISA Kit according to instructions of the manufacturer.

FIG. 8A shows the effect of IgG on the levels of p44/42 MAPK at Thr202/Tyr204 in CHO cells expressing mGlu7 receptors. The p44/42 MAPK levels were determined by means of PathScan™ Sandwich ELISA Kit according to instructions of the manufacturer. The IgG-induced increase of p44/42 MAPK levels is transient reaching a maximal level 5 min after treatment and rapidly declines thereafter.

Figure 8B:
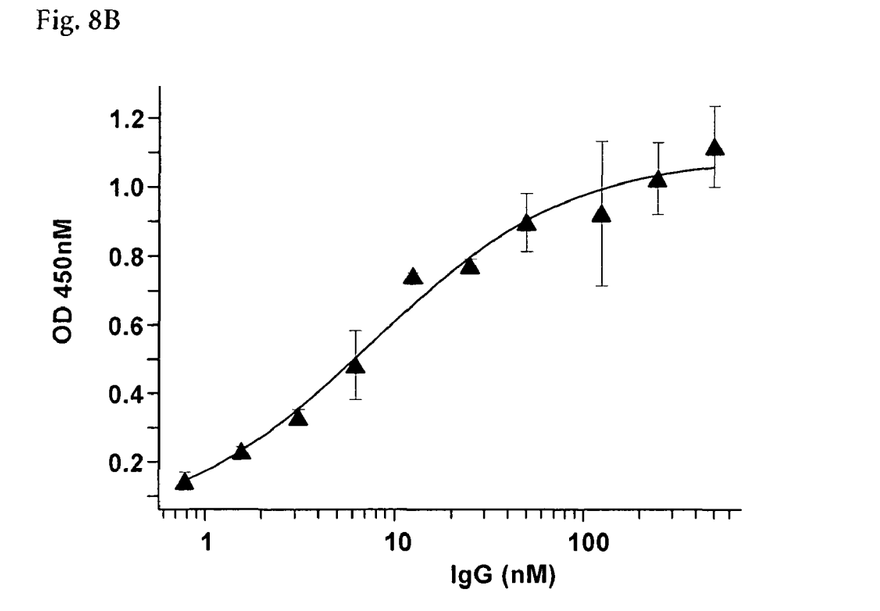
FIG. 8B shows that increasing doses of IgG induces saturable levels of p44/42 MAPK 5 min after treatment of CHO cells expressing mGlu7 receptors. The potency of the IgG in triggering p44/42 MAPK activities is in the same order of magnitude as the potency in inhibiting the L-AP4-induced inhibition of foskolin activities as shown in FIG. 4.

FIG. 8B shows that increasing doses of IgG induces saturable levels of p44/42 MAPK 5 min after treatment of CHO cells expressing mGlu7 receptors. The potency of the IgG in triggering p44/42 MAPK activities is in the same order of magnitude as the potency in inhibiting the L-AP4-induced inhibition of foskolin activities as shown in FIG. 4.

Figure 8C:
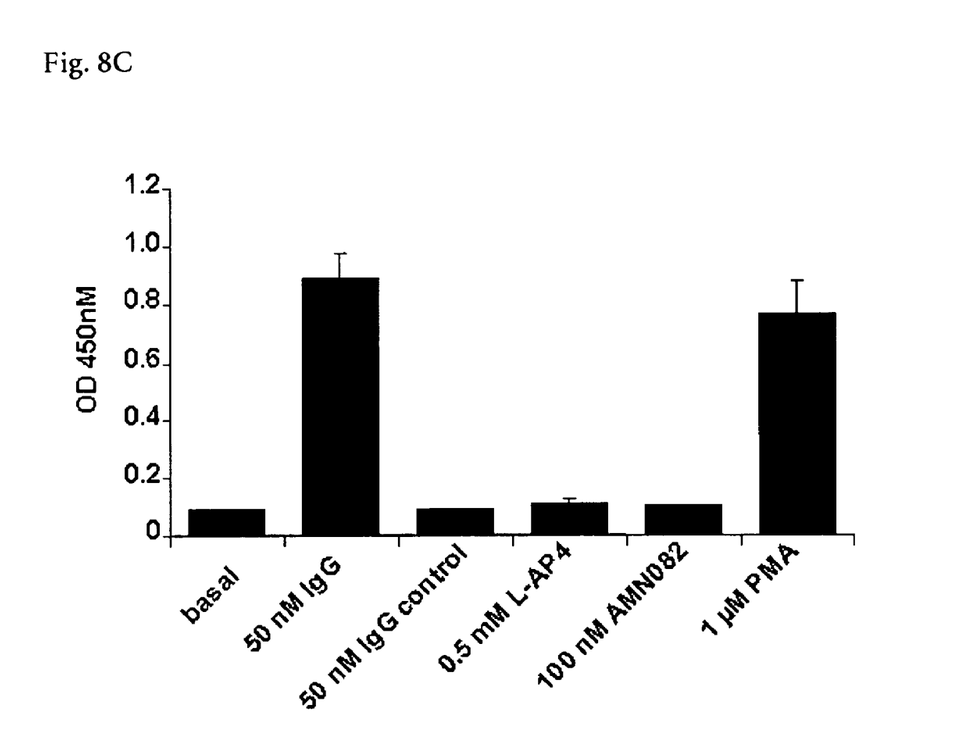
FIG. 8C shows the specificity of the IgG-induced levels of p44/42 MAPK activity after treatment of CHO cells expressing mGlu7 receptors. In comparison to the IgG, a anti 6×His IgG, the orthosteric mGlu7 agonist L-AP4 and the allosteric mGlu7 agonist AMN082 do not trigger increases of p44/42 MAPK activities. The efficacy of p44/42 MAPK activities was comparable to the levels obtained with the positive control PMA.

FIG. 8C shows the specificity of the IgG-induced levels of p44/42 MAPK activity after treatment of CHO cells expressing mGlu7 receptors. In comparison to the IgG, a anti 6×His IgG, the orthosteric mGlu7 agonist L-AP4 and the allosteric mGlu7 agonist AMN082 do not trigger increases of p44/42 MAPK activities. The efficacy of p44/42 MAPK activities was comparable to the levels obtained with the positive control PMA.

Figure 8D:
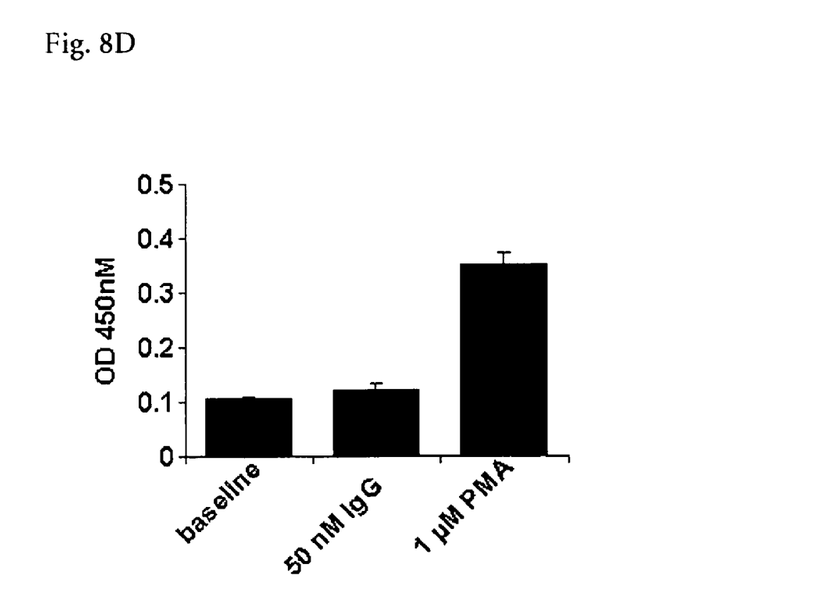
FIG. 8D shows the absence p44/42 MAPK activity after treatment of non-transfected CHO cells with the IgG in comparison to the activity obtained with the positive control PMA, suggesting a mGlu7-specific activity of the IgG.

FIG. 8D shows the absence p44/42 MAPK activity after treatment of non-transfected CHO cells with the IgG in comparison to the activity obtained with the positive control PMA, suggesting a mGlu7-specific activity of the IgG.

EXAMPLE 7 siRNA Preparation

Oligoribonucleotide Synthesis

Oligoribonucleotides were synthesized according to the phosphoramidite technology on solid phase employing an ABI 394 synthesizer (Applied Biosystems) at the 10 µmol scale. For RNA sequence information see table 1. Syntheses were performed on a solid support made of controlled pore glass (CPG, 520 Å, with a loading of 75 µmol/g, obtained from Prime Synthesis, Aston, Pa., USA). Regular RNA phosphoramidites, 2'-β-Methylphosphoramidites as well as ancillary reagents were purchased from Proligo (Hamburg, Germany). Specifically, the following amidites were used: (5'-β-dimethoxytrityl-$N^6$-(benzoyl)-2'-O-t-butyldimethylsilyl-adenosine-3'-O-(2-cyanoethyl-N,N-diisopropylamino) phosphoramidite, 5'-O-dimethoxytrityl-$N^4$-(acetyl)-2'-O-t-butyldimethylsilyl-cytidine-3'-O-(2-cyanoethyl-N,N-diisopropylamino) phosphoramidite, (5'-O-dimethoxytrityl-$N^2$-(isobutyryl)-2'-O-t-butyldimethylsilyl-guanosine-3'-O—(2-cyanoethyl-N,N-diisopropylamino) phosphoramidite, and 5'-O-dimethoxytrityl-2'-O-t-butyldimethylsilyl-uridine-3'-O-(2-cyanoethyl-N,N-diisopropylamino) phosphoramidite. 2'-O-Methylphosphoramidites carried the same protecting groups as the regular RNA amidites with the exception of 2'-O-methyl-cytidine which was $N^4$-(t-butylphenoxyacetyl) protected. All amidites were dissolved in anhydrous acetonitrile (100 mM) and molecular sieves (3 Å) were added. To generate the sulfhydryl linker at the 3'-end of the oligomer the 1-O-Dimethoxytrityl-hexyl-disulfide, 1'-[(2-cyanoethyl)-(N,N-diisopropyl)]-phosphoramidite linker from Glen Research (Sterling, Va., USA) was used. Without any modification of the synthesis cycle the Cy5 fluorescent dye was attached to the 5'-end using the corresponding phosphoramidite (obtained from GE Healthcare, Munich Germany). 5-Ethyl thiotetrazole (ETT, 500 mM in acetonitrile) was used as activator solution. Coupling times were 6 minutes. In order to introduce phosphorothioate linkages a 100 mM solution of 3-ethoxy-1,2,4-dithiazoline-5-one (EDITH, obtained from Link Technologies, Lanarkshire, Scotland) in anhydrous acetonitrile was employed.

Cleavage and Deprotection of Support Bound Oligomer

After finalization of the solid phase synthesis, the dried solid support was transferred to a 15 mL tube and treated with methylamine in methanol (2M, Aldrich) for 180 min at 45° C. After centrifugation the supernatant was transferred to a new 15 mL tube and the CPG was washed with 1200 µL N-methylpyrrolidin-2-one (NMP, Fluka, Buchs, Switzerland). The washing was combined with the methanolic methylamine solution and 450 µL Triethylamine trihydrofluoride (TEA.3HF, Alfa Aesar, Karlsruhe, Germany) was added. This mixture was brought to 65° C. for 150 min. After cooling to rt 0.75 mL NMP and 1.5 mL of ethoxytrimethylsilane (Fluka, Buchs, Switzerland) was added. 10 min later, the precipitated oligoribonucleotide was collected by centrifugation, the supernatant was discarded and the solid was reconstituted in 1 mL buffer A (see below).

Purification of Oligoribonucleotides

Crude oligomers were purified by RP HPLC using a XTerra Prep MS C8 10×50 mm column (Waters, Eschborn, Germany) on an AKTA Explorer system (GE Helthcare). Buffer A was 100 mM triethylammonium acetate (Biosolve, Valkenswaard, The Netherlands) and buffer B contained 50% acetonitrile in buffer A. A flow rate of 5 mL/min was employed. UV traces at 260, 280 and 643 nm were recorded. A gradient of 5% B to 60% B within 58 column volumes (CV) was employed. Appropriate fractions were pooled and precipitated with 3M NaOAc, pH=5.2 and 70% Ethanol.

Finally, the purified oligomer was desalted by size exclusion chromatography on a column containing Sephadex G-25 (GE Healthcare). The concentration of the solution was determined by absorbance measurement at 260 nm in a UV photometer (Beckman Coulter, Krefeld, Germany). Until annealing the individual strands were stored as frozen solutions at −20° C.

Annealing of oligoribonucleotides to generate siRNA

Complementary strands were annealed by combining equimolar RNA solutions. The mixture was lyophilized and reconstituted with an appropriate volume of annealing buffer (100 mM NaCl, 20 mM sodium phosphate, pH 6.8) to achieve the desired concentration. This solution was placed into a water bath at 95° C. which was cooled to rt within 3h.

siRNA sequence information

```
                                          (SEQ ID NO: 1)
sense strand (5'--3'):
(Cy5)cuuAcGcuGAGuAcuucGAdTdT(C6SSC6)dT (SEQ ID NO: 2)
antisense strand (5'--3'):
UCGAAGuACUcAGCGuAAGdTsdT lower case letters: 2'OMe nucleotide;
s: phosphorothioate linkage;
dT: deoxythymidine
``` lower case letters: 2'OMe nucleotide; s: phosphorothioate linkage; dT: deoxythymidine

EXAMPLE 8

Antibody-siRNA Conjugate Preparation

Maleimide activation of the antibody: The monoclonal antibody mGluR7-CHO-1/28 was reacted with a 10-fold molar excess of the SMCC (sulfosuccinimidyl 4-[N maleimidomethyl]cyclohexane-1-carboxylate), followed by removal of excess (nonreacted) reagent by desalting.

siRNA activation: The Cy5 labeled siRNA having a C6SSC6-Linker to a single deoxythymidine was reduced with TCEP (Tris[2-carboxyethyl]phosphine) to selectively reduce the disulfide bonds.

The sulfhydryl-containing siRNA was then added to react with the maleimide groups already attached to the monoclonal antibody. Unreacted free sulfhydryls on siRNA were then blocked using NEM (N-Ethylmaleimide) and the final product purified by size exlusion chromatography on a Superdex 200 HR 10/30 column.

The final labeling-ratio is determined with the nanodrop (IgG adsorption at 280 nm, Cy5 at 646 nm, Extinctioncoefficient Cy5: 250,000).

Plasticware, Solutions and Reagents

| | |
|---|---|
| Assay plate | Costar 96 well Special Optics plate, catalog nr 3614 |
| 10× HBSS | GIBCO catalog No. 14065-049 |
| Hepes | 1 M solution, GIBCO catalog No. 15630-056 |
| BSA | bovine serum albumine fraction V, Sigma, catalog No. A-3059 |
| Hoechst 33258 | Sigma # B-2261 (bisBenzimide), dissolved to 10 mM in DMSO. |
| TrueBlue Chloride | Molecular Probes Catalog nr T1323, dissolved to 2 mM in 1:2 MeOH:DMSO |
| CellMask Blue | 5mg/ml in DMSO, Invitrogen catalog no H34558 |
| Formaldehyde | 4%, diluted from 36.5% stock (Fluka, catalog No. 47629) in PBS. |
| Goat anti mouse Alexa | 488 antibody: 1µg/µl solution Invitrogen catalog no A11029 |
| Goat anti mouse Alexa | 532 antibody: 1µg/µl solution Invitrogen catalog no A11200A |
| Goat anti mouse Alexa | 647 antibody: 1µg/µl solution Invitrogen catalog no A21235A |
| Triton X-100: | Fluka catalog no 93426, diluted to 4% vol/vol in PBS |
| Goat serum: | Sigma Catalog No G9023 |
| Pertussis toxin: | Sigma Catalog No P-2980. Stock: 0.2 mg/ml in 50% glycerol, 0.5M NaCl, 50 mM Tris-Glycine |
| Krebs Ringer | Sigma # K-4002, |
| L-AP4 | Tocris # 0103 |
| Forskolin | Sigma # F 3917 |
| IBMX | Sigma |
| Lysis reagent | Tris, NaCl, 1.5% Triton X100, 2.5% NP40, 10% NaN3 |
| Detection solution | 20 µM mAb Alexa700-cAMP 1:1, and 48 Ruthenium-2-AHA-cAMP |
| Growth medium | DMEM (Invitrogen No 31331), 1× HT supplement, 10% FCS |
| Opti-MEM | Invitrogen # 11058-021 |
| Lipofectamine plus | Invitrogen |
| pcDNA3.1(+) | Invitrogen |
| CHO-dhfr- | ATCC No CRL-9096 |
| Assay buffer | 5 mM KCL, 154 mM NaCl, 2.3 mM CaCl2, 5 mM NaHCO3, 1 mM MgCl2, 5.5 mM Glucose, 5 mM Hepes, 10 µM IBMX, pH 7.4 |
| Lysis buffer | 25 mM Tris, 0.4 mM DTT, 0.4 mM CDTA, 0.2% glycerol, 0.2% Triton X-100, pH 7.8 |
| PMA | Phorbol 12-Myristate 13-Acetate (Sigma # P8139) |
| AMN082 | Dibenzhydrylethane-1,2-diamine dihydrochloride, in-house synthesis |
| PathScan ™ | Sandwich ELISA Kit # 7315, Cell Signaling, Beverly, MA |
| fatty acid free BSA | Sigma # A-6003-25G |

While there are shown and described presently preferred embodiments of the invention, it is to be distinctly understood that the invention is not limited thereto but may be otherwise variously embodied and practiced within the scope of the following claims.

The invention claimed is:

1. An antibody produced by hybridoma cell line mGluR7-CHO-1/28 deposited under accession number DSM ACC2855.

2. A conjugate comprising the antibody of claim 1 and an active compound covalently linked to the antibody.

3. The conjugate of claim 2, wherein the active compound is a toxin or a small interfering RNA (siRNA) molecule.

4. A pharmaceutical composition comprising the antibody of claim 1 or conjugate of claim 3 and a pharmaceutically acceptable carrier.

* * * * *